(12) United States Patent
Luo et al.

(10) Patent No.: US 11,515,488 B2
(45) Date of Patent: Nov. 29, 2022

(54) THERMALLY ACTIVATED DELAYED FLUORESCENCE MATERIAL HAVING RED, GREEN, OR BLUE COLOR, SYNTHESIS METHOD THEREOF, AND APPLICATION THEREOF

(71) Applicant: WUHAN CHINA STAR OPTOELECTRONICS SEMICONDUCTOR DISPLAY TECHNOLOGY CO., LTD., Wuhan (CN)

(72) Inventors: Jiajia Luo, Wuhan (CN); Xianjie Li, Wuhan (CN); Jinchang Huang, Wuhan (CN); Yu Gu, Wuhan (CN); Lin Yang, Wuhan (CN); Yamei Bai, Wuhan (CN)

(73) Assignee: WUHAN CHINA STAR OPTOELECTRONICS SEMICONDUCTOR DISPLAY TECHNOLOGY CO., LTD., Wuhan (CN)

( * ) Notice: Subject to any disclaimer, the term of this patent is extended or adjusted under 35 U.S.C. 154(b) by 405 days.

(21) Appl. No.: 16/622,954

(22) PCT Filed: Sep. 26, 2019

(86) PCT No.: PCT/CN2019/108031
§ 371 (c)(1),
(2) Date: Dec. 16, 2019

(87) PCT Pub. No.: WO2021/000434
PCT Pub. Date: Jan. 7, 2021

(65) Prior Publication Data
US 2021/0408394 A1   Dec. 30, 2021

(30) Foreign Application Priority Data
Jul. 3, 2019   (CN) .......................... 201910592316.7

(51) Int. Cl.
*H01L 51/00* (2006.01)
*C07C 225/22* (2006.01)
(Continued)

(52) U.S. Cl.
CPC ........ *H01L 51/0072* (2013.01); *C07C 225/22* (2013.01); *C07D 209/86* (2013.01); *C07D 265/38* (2013.01); *C09K 11/06* (2013.01); *H01L 51/0059* (2013.01); *H01L 51/0071* (2013.01); *C09K 2211/1007* (2013.01); *C09K 2211/1014* (2013.01); *C09K 2211/1018* (2013.01); *H01L 51/5012* (2013.01); *H01L 51/5016* (2013.01); *H01L 2251/552* (2013.01)

(58) Field of Classification Search
CPC ............ H01L 51/0072; H01L 51/0059; H01L 51/0071; H01L 51/5012; H01L 51/5016; H01L 2251/552; C07C 225/22; C07D 209/86; C07D 265/38; C09K 11/06; C09K 2211/1007; C09K 2211/1014; C09K 2211/1018
See application file for complete search history.

(56) References Cited

U.S. PATENT DOCUMENTS

2018/0297950 A1* 10/2018 Li ......................... C07D 265/38
2020/0194682 A1*  6/2020 Luo ...................... C07D 219/14
(Continued)

FOREIGN PATENT DOCUMENTS

CN           105694859 A     6/2016
CN           110272377 A     9/2019
(Continued)

OTHER PUBLICATIONS

R. Dorel et al., 58 Angew. Chem. Int. Ed., 17118-17129 (Jun. 5, 2019) (Year: 2019).*
(Continued)

*Primary Examiner* — Alexander R Pagano
(74) *Attorney, Agent, or Firm* — PV IP PC; Wei Te Chung; Ude Lu

(57) ABSTRACT

The present disclosure relates to the field of organic light-emitting materials, and more particularly, to a thermally activated delayed fluorescence material having red, green, or blue color, a synthesis method thereof, and application thereof. The thermally activated delayed fluorescence material having red, green, or blue color has the following structural formula:

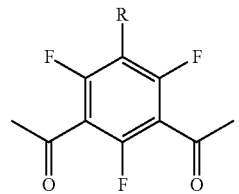

the present disclosure provides a novel thermally activated delayed fluorescence material having red, green, or blue color which has a lower singlet triplet energy level difference, a high RISC rate constant (kRISC), and a high photoluminescence quantum yield (PLQY). It has significant characteristics of a thermally activated delayed fluorescence material and a long service life that can be used in an electroluminescent display and a light-emitting equipment structure which are mass produced.

7 Claims, 2 Drawing Sheets

(51) Int. Cl.
  *C07D 209/86*  (2006.01)
  *C07D 265/38*  (2006.01)
  *C09K 11/06*  (2006.01)
  *H01L 51/50*  (2006.01)

(56) References Cited

U.S. PATENT DOCUMENTS

2020/0251662 A1*   8/2020   Bai ..................... H01L 51/0035
2021/0296586 A1*   9/2021   Wang ................... C07C 221/00

FOREIGN PATENT DOCUMENTS

JP     2017149888 A   *   8/2017
JP     2017149888 A     8/2017

OTHER PUBLICATIONS

Pan, Jiunn-Hung; et al. Theoretical investigations of triphenylamine derivatives as hole transporting materials in OLEDs: Correlation of the Hammett parameter of the substituent to ionization potential, and reorganization energy level. Computational Materials Science, 2006 vol. 38 ; Dec. 31, 2006; p. 105-112.

* cited by examiner

THERMALLY ACTIVATED DELAYED FLUORESCENCE MATERIAL HAVING RED, GREEN, OR BLUE COLOR, SYNTHESIS METHOD THEREOF, AND APPLICATION THEREOF

CROSS-REFERENCE TO RELATED APPLICATIONS

This is the U.S. National Stage of International Patent Application No. PCT/CN2019/108031 filed on Sep. 26, 2019 which in turn claims the benefit of Chinese Patent Application No. 201910592316.7 filed on Jul. 3, 2019.

FIELD OF INVENTION

The present disclosure relates to the field of organic light-emitting materials, and more particularly, to a thermally activated delayed fluorescence material having red, green, or blue color, a synthesis method thereof, and application thereof.

BACKGROUND OF INVENTION

Organic light-emitting diodes (OLEDs) are sandwich type devices constituted by a structure of electrode/light-emitting layer/electrode, which was invented by American-Chinese professor Deng Qingyun et al. When current passes, a strong electric field will drive the organic light-emitting layer between the electrodes of a device to emit light. Based on electroluminescence phenomenon of OLEDs, OLEDs are widely used in fields of information display and solid-state lighting.

Continuous updating of organic light-emitting materials has greatly promoted development of OLED technology. In general, fluorescent materials are the first generation, and transition metal complex phosphorescent materials are the second generation. The fluorescent materials as the first generation have longer service lives, but have low luminous efficiency; ratio of excitons in singlet and triplet states is 1:3, and theoretical upper limit of internal quantum efficiency is only 25% in OLEDs, thereby greatly limiting applications of fluorescent electroluminescent devices. Singlet state of the transition metal complex phosphorescent materials as the second generation can be transferred to triplet state by intersystem crossing (ISC), and internal quantum efficiency thereof is close to 100%. However, phosphorescent materials need to be doped with noble rare metals such as Ir and Pt, which have higher material costs and shorter service lives.

Thermally activated delayed fluorescence (TADF) materials are new type organic light-emitting materials which have low cost and high efficiency, and are called the third generation organic light-emitting materials. Through ingenious molecular designs, the molecule has a lower minimum singlet triplet energy level difference ($\Delta E_{ST}$), which can convert triplet excitons into singlet exciton radiation to emit light by thermal excitation reverse intersystem crossing, thereby breaking through the theoretical limit of 25% utilization rate of traditional fluorescent materials and achieving 100% luminescence quantum efficiency. Due to involvement of excitons in the process of reverse intersystem crossing from triplet state to singlet state, TADF materials usually exhibit photochemical long-lived fluorescence (delayed fluorescence). Lifetime of delayed fluorescence can be on order of microseconds to milliseconds, significantly different from traditional fluorescent materials. TADF materials combine advantages of good stability of organic fluorescent materials and high luminous efficiency of transition metal complex phosphorescent materials, have wide applications, and are one of current research hotspots.

Technical Problem for thermally activated delayed fluorescence materials, a high RISC rate constant (kRISC) and a high photoluminescence quantum yield (PLQY) are necessary conditions for preparing high efficiency OLEDs. For now, a thermally activated delayed fluorescence material having a high kRISC and a high PLQY at the same time and a thermally activated delayed fluorescence material having red, green, or blue color that can be used in a mass produced organic light-emitting device structure have yet to be developed.

SUMMARY OF INVENTION

An objective of the present disclosure is to provide a thermally activated delayed fluorescence material having red, green, or blue color, to have high luminous efficiency and long service life.

To achieve the above objective, the present disclosure provides following technical solutions:

A thermally activated delayed fluorescence material having red, green, or blue color, having the following structural formula:

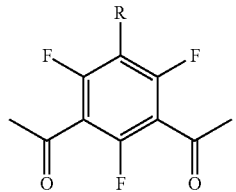

wherein, R is one of the following structural formulas:

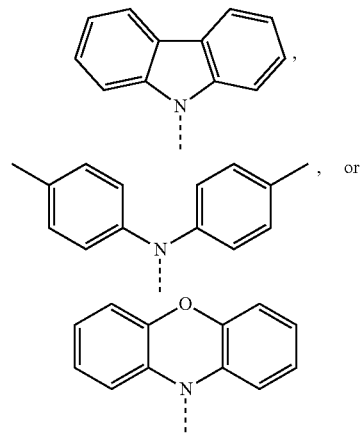

Another objective of the present disclosure is to provide a synthesis method of the above thermally activated delayed fluorescence material having red, green, or blue color. The method comprises following steps: under an inert gas environment, a Buchwald-Hartwig coupling reaction between a raw material 1 and a raw material 2 is performed under an effect of a palladium catalyst to obtain the thermally activated delayed fluorescence material having red, green, or blue color;

wherein, the raw material 1 has the following structural formula:

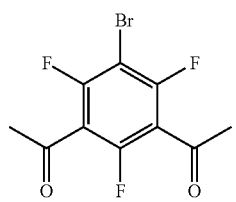

the raw material 2 is one of carbazole, phenoxazine, or dimethyldiphenylamine; a molar ratio of the raw material 1 to the raw material 2 ranges from 1:1 to 1:3.

Preferably, a reaction temperature of the Buchwald-Hartwig coupling reaction ranges from 80° C. to 160° C., and a reaction time thereof ranges from 12 hours to 48 hours.

Preferably, a reaction solvent of the Buchwald-Hartwig coupling reaction is dehydrated and deoxygenated toluene; and the palladium catalyst is at least one selected from the group consisting of palladium acetate, palladium nitrate, palladium sulfate, or palladium chloride.

Preferably, after finishing the Buchwald-Hartwig coupling reaction, a reaction product is subjected to cooling, extraction, and column chromatography separation in sequence to obtain the thermally activated delayed fluorescence material having red, green, or blue color.

Another objective of the present disclosure is to provide an application of the above thermally activated delayed fluorescence material having red, green, or blue color, or an application of the thermally activated delayed fluorescence material having red, green, or blue color prepared by the above synthesis method in organic electroluminescence. Specifically, the thermally activated delayed fluorescence material having red, green, or blue color in the present disclosure can be directly used in a light-emitting layer of an electrothermally activated delayed fluorescent device. It also can be used as a light-emitting guest material which is doped into an energy matching host material and constitutes a light-emitting layer of an electroluminescent device, or a blue thermally activated delayed fluorescence material is as a light-emitting host material to dope into an energy matching guest material and constitutes a light-emitting layer of an electroluminescent device.

Specifically, the electrothermally activated delayed fluorescent device comprises a substrate layer, a light-emitting layer, and a cathode layer in a stack, and a light-emitting material for the light-emitting layer is the above thermally activated delayed fluorescence material having red, green, or blue color or the thermally activated delayed fluorescence material having red, green, or blue color prepared by the above synthesis method.

Preferably, the electrothermally activated delayed fluorescent device further comprises a hole injection layer disposed on the substrate layer, a transport layer disposed on the hole injection layer, and an electron transport layer disposed between the light-emitting layer and the cathode layer.

The present disclosure further provides a light-emitting device which comprises the above electrothermally activated delayed fluorescent device.

Beneficial effect: the present disclosure provides a novel thermally activated delayed fluorescence material having red, green, or blue color which has a lower single triplet energy level difference, a high RISC rate constant (kRISC), and a high photoluminescence quantum yield (PLQY). It has significant characteristics of a thermally activated delayed fluorescence material and a long service life that can be used in an electroluminescent display and a light-emitting equipment structure which are mass produced. Besides, the synthesis method provided by the present disclosure is easy to perform and has a high synthetic efficiency.

DESCRIPTION OF DRAWINGS

The accompanying figures to be used in the description of embodiments of the present disclosure or prior art will be described in brief to more clearly illustrate the technical solutions of the embodiments or the prior art. The accompanying figures described below are only part of the embodiments of the present disclosure, from which those skilled in the art can derive further figures without making any inventive efforts.

DETAILED DESCRIPTION OF PREFERRED EMBODIMENTS

Figure 1:
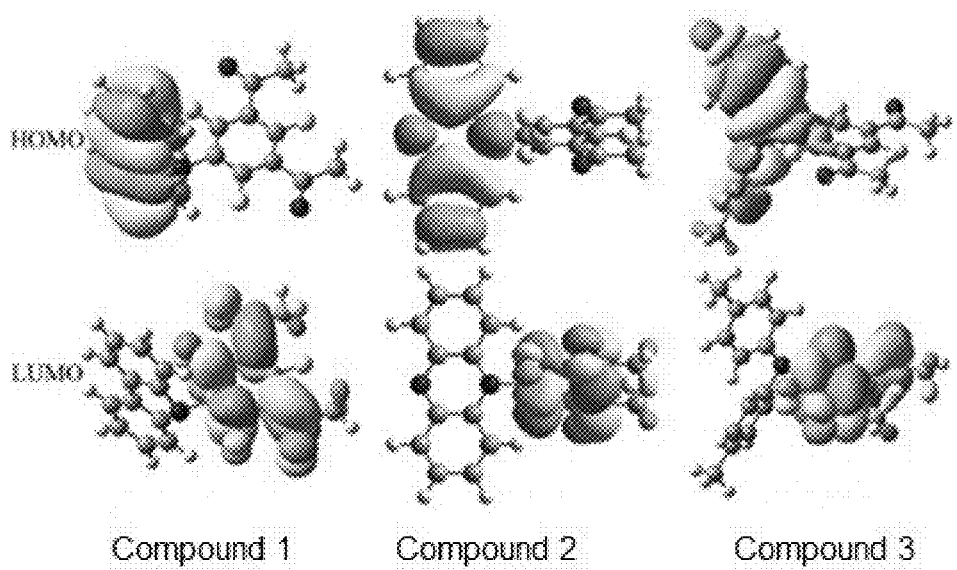
FIG. 1 is a schematic molecular orbital diagram of compound 1 to compound 3 obtained according to embodiment 1 to embodiment 3 of the present disclosure.

The present disclosure will be further described below in conjunction with embodiments 1 to 3 and application embodiments 1 to 3.

Embodiment 1: Synthesis of a Thermally Activated Delayed Fluorescence Material Having Red, Green, or Blue Color The reaction formula is as follows:

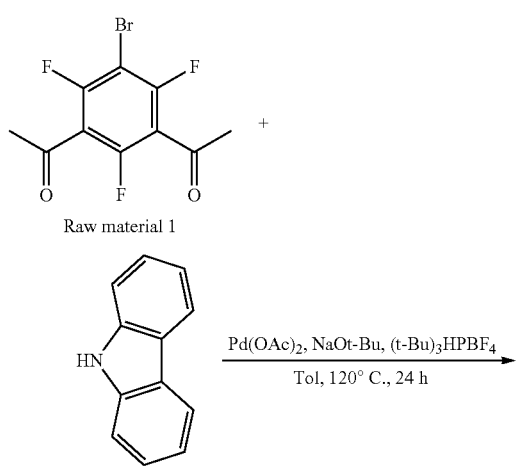

-continued

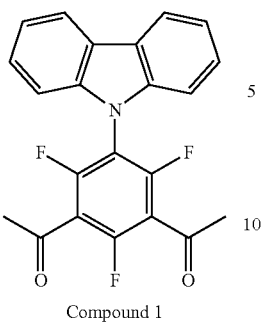

Compound 1

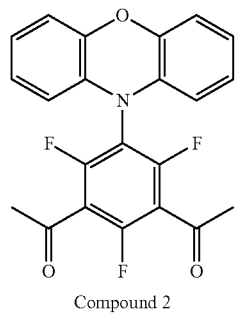

Compound 2

Add raw material 1 (1.47 g, 5 mmol), carbazole (1.00 g, 6 mmol), palladium acetate (45 mg, 0.2 mmol), and tri-tert-butylphosphine tetrafluoroborate (0.17 g, 0.6 mmol) to a 100 mL two-necked flask, then add NaOt-Bu (0.58 g, 6 mmol) in the glove box, then inject 40 mL of toluene which is dehydrated and deoxygenated under an argon atmosphere, and then react at 120° C. for 24 hours. Cool to room temperature, the reaction solution is poured into 200 mL of ice water, and is extracted three times with dichloromethane. Combine the organic phase to spin to a silica gel column chromatography (volume of dichloromethane:volume of n-hexane, 2:1) to separate and purify to obtain 1.6 g of white blue powders. The yield is 84%.

The nuclear magnetic resonance spectrum of the obtained product (compound 1) is: 1H NMR (300 MHz, CD2Cl2, δ): 8.55 (d, J=6.9 Hz, 2H), 7.93 (d, J=6.0 Hz, 2H), 7.35-7.18 (m, 4H), 2.50 (s, 6H). MS (EI) m/z: [M]+ calcd for C22H14F3NO2, 381.10; found, 381.08.

Add raw material 1 (1.47 g, 5 mmol), phenoxazine (1.01 g, 6 mmol), palladium acetate (45 mg, 0.2 mmol), and tri-tert-butylphosphine tetrafluoroborate (0.17 g, 0.6 mmol) to a 100 mL two-necked flask, then add NaOt-Bu (0.58 g, 6 mmol) in the glove box, then inject 40 mL of toluene which is dehydrated and deoxygenated under an argon atmosphere, and then react at 120° C. for 24 hours. Cool to room temperature, the reaction solution is poured into 200 mL of ice water, and is extracted three times with dichloromethane. Combine the organic phase to spin to a silica gel column chromatography (volume of dichloromethane:volume of n-hexane, 2:1) to separate and purify to obtain 1.5 g of green powders. The yield is 76%.

The nuclear magnetic resonance spectrum of the obtained product (compound 2) is: 1H NMR (300 MHz, CD2Cl2, δ): 7.14 (d, J=6.3 Hz, 2H), 7.05-6.96 (m, 6H), 2.50 (s, 6H). MS (EI) m/z: [M]+ calcd for C22H14F3NO3, 397.09; found, 397.08.

Embodiment 2: Synthesis of a Thermally Activated Delayed Fluorescence Material Having Red, Green, or Blue Color The reaction formula is as follows:

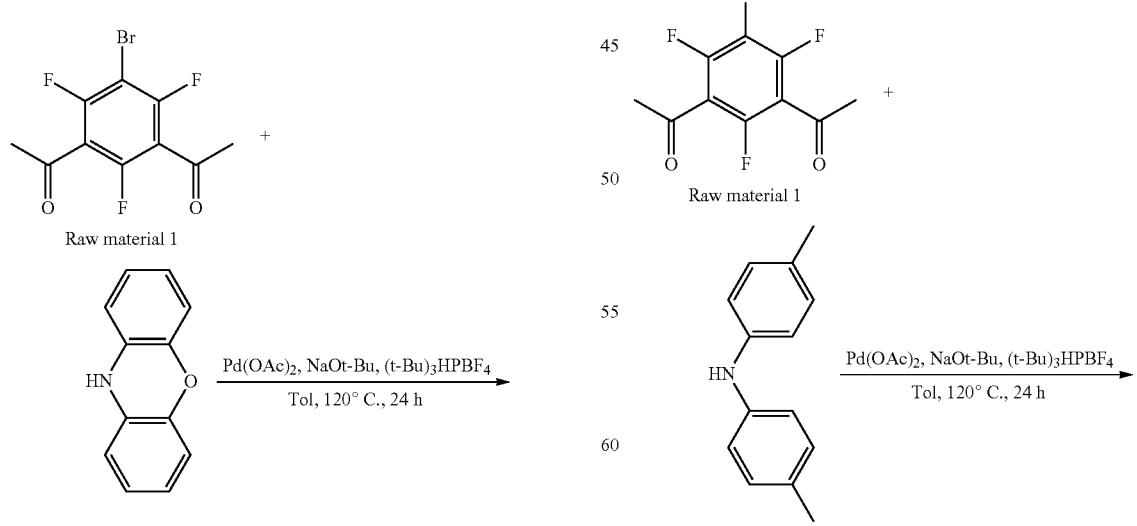

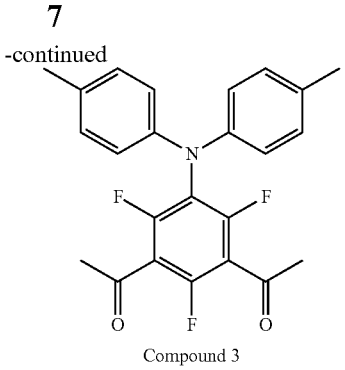

Compound 3

The reaction formula is as follows:

Add raw material 1 (1.47 g, 5 mmol), dimethyldiphenylamine (1.10 g, 6 mmol), palladium acetate (45 mg, 0.2 mmol), and tri-tert-butylphosphine tetrafluoroborate (0.17 g, 0.6 mmol) to a 100 mL two-necked flask, then add NaOt-Bu (0.58 g, 6 mmol) in the glove box, then inject 40 mL of toluene which is dehydrated and deoxygenated under an argon atmosphere, and then react at 120° C. for 24 hours. Cool to room temperature, the reaction solution is poured into 200 mL of ice water, and is extracted three times with dichloromethane. Combine the organic phase to spin to a silica gel column chromatography (volume of dichloromethane:volume of n-hexane, 2:1) to separate and purify to obtain 1.6 g of red powders. The yield is 76%.

The nuclear magnetic resonance spectrum of the obtained product (compound 2) is: 1H NMR (300 MHz, CD2Cl2, δ): 7.15 (d, J=6.9 Hz, 4H), 7.09 (d, J=6.6 Hz, 2H), 2.50 (s, 6H), 2.32 (s, 6H). MS (EI) m/z: [M]+ calcd for C22H20F3NO2, 381.10; found, 381.08.

The molecular orbital diagram of compound 1 to compound 3 obtained according to embodiment 1 to embodiment 3 of the present disclosure is as shown in FIG. 1. The distribution of HOMO and LUMO of compound 1 to compound 3 can be seen from FIG. 1. Specifically, HOMO is distributed on electron donors, LUMO is distributed on electron acceptors, and there is great HOMO-LUMO separation, thereby ensuring molecules have a lower singlet triplet energy level difference.

Electrochemical energy levels and other parameters of compounds 1 to 3 obtained according to embodiments 1 to 3 are tested, the result are as shown in the following table 1: S1 was determined by a room temperature fluorescence spectroscopy, T1 was determined by a low temperature (77K) phosphorescence spectrometer, and HOMO and LUMO were determined by electrochemical redox.

TABLE 1 the lowest singlet state (S1), the lowest triplet state (T1), and electrochemical energy levels of compound 1 to compound 3.

|  | PL Peak (nm) | $S_1$ (eV) | $T_1$ (eV) | $\Delta E_{ST}$ (eV) | HOMO (eV) | LUMO (eV) |
| --- | --- | --- | --- | --- | --- | --- |
| Compound 1 | 460 | 2.70 | 2.62 | 0.08 | −6.11 | −2.48 |
| Compound 2 | 543 | 2.29 | 2.18 | 0.11 | −5.62 | −2.48 |
| Compound 3 | 638 | 1.95 | 1.76 | 0.19 | −5.43 | −2.48 |

Figure 2:
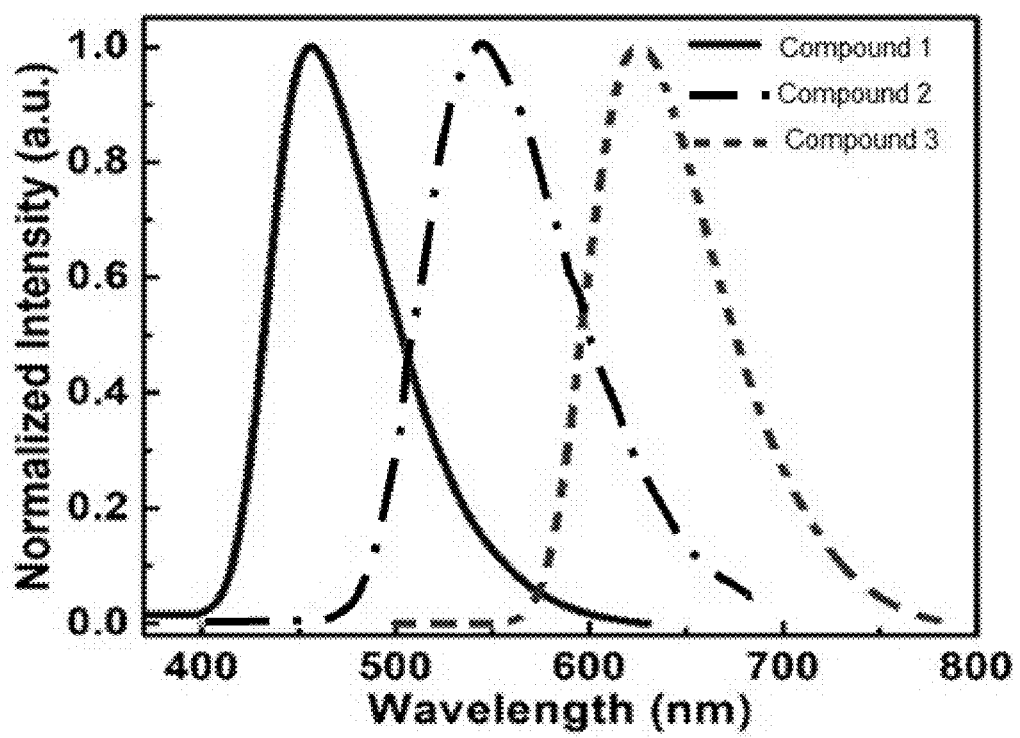
FIG. 2 is photoluminescence spectrums of compound 1 to compound 3 in a n-hexane solution at room temperature obtained according to embodiment 1 to embodiment 3 of the present disclosure.

Results of photoluminescence spectrums of compound 1 to compound 3 in a n-hexane solution at room temperature obtained according to embodiment 1 to embodiment 3 are as shown in FIG. 2. In FIG. 2, waveforms from left to right are respectively photoluminescence spectrums of compound 1, compound 2, and compound 3. It can be known from FIG. 2: as the electron donating ability of the electron donor increases, the charge-transfer state energy of the luminescent molecule is lower and the corresponding spectrum is gradually red-shifted.

Application Embodiment 1: An Electrothermally Activated Delayed Fluorescent Device 1

An electrothermally activated delayed fluorescent device can be prepared according to methods known in the art, such as a method disclosed in the reference of Adv. Mater. 2003, 15, 277. The specific method is: vapor depositing HATCN, TCTA, host material: TADF guest, TmPyPB, 1 nm of LiF, and 100 nm of Al on a cleaned conductive glass substrate (ITO) under a high vacuum condition in sequence.

Figure 3:
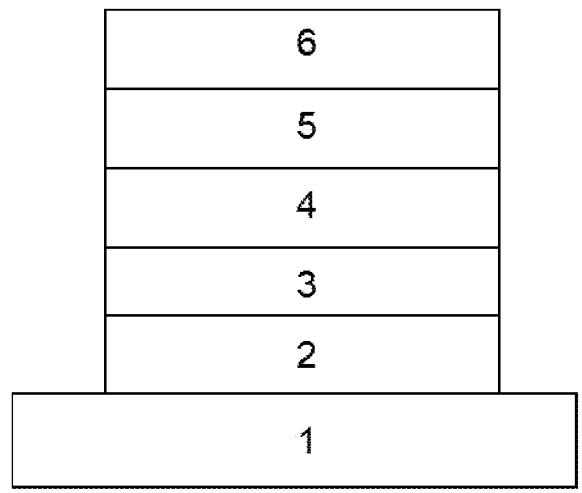
FIG. 3 is a schematic structural diagram of an electrothermally activated delayed fluorescent device according to an application embodiment of the present disclosure.

A structure of the electrothermally activated delayed fluorescent device is as shown in FIG. 3, which comprises: a substrate layer 1, a hole injection layer 2 disposed on the substrate layer 1, a transport layer 3 disposed on the hole injection layer 2, a light-emitting layer 4 disposed on the transport layer 3, an electron transport layer 5 disposed on the light-emitting layer 4, and a cathode layer 6 disposed on the electron transport layer 5. The substrate layer 1 is a glass or a conductive glass (ITO), the hole injection layer 2 is made of HATCN, the transport layer 3 is made of Tris(4-carbazoyl-9-ylphenyl)amine (TCTA), the light-emitting layer 4 is made of the compound 1 obtained according to embodiment 1, the transport layer 5 is made of 1,3,5-tris(3-(3-pyridyl)phenyl)benzene (TmPyPB), and the cathode layer 6 is made of lithium fluoride/aluminum. The structure of formed device 1 is: ITO/HATCN (2 nm)/TCTA (35 nm)/DPEPO: compound 1 (2%, 20 nm)/TmPyPB (40 nm)/LiF (1 nm)/Al (100 nm).

Application Embodiment 2: An Electrothermally Activated Delayed Fluorescent Device 2

Application embodiment 2 uses the same method as application embodiment 1. The difference is that the light-emitting layer 4 is made of the compound 2 obtained according to embodiment 2. A structure of formed device 2 is: ITO/HATCN (2 nm)/TCTA (35 nm)/mCBP: compound 2 (6%, 40 nm)/TmPyPB (40 nm)/LiF (1 nm)/Al (100 nm).

Application Embodiment 3: An Electrothermally Activated Delayed Fluorescent Device 3

Application embodiment 3 uses the same method as application embodiment 1. The difference is that the light-emitting layer 4 is made of the compound 3 obtained according to embodiment 3. A structure of formed device 3 is: ITO/HATCN (2 nm)/TCTA (35 nm)/CBP: compound 3 (10%, 40 nm)/TmPyPB (40 nm)/LiF (1 nm)/Al (100 nm).

Performances of the devices 1 to 3 obtained according to application embodiments 1 to 3 are tested. Current-brightness-voltage characteristics of the device are measured by Keithley source measurement system with a calibrated silicon photodiode (Keithley 2400 Sourcemeter, Keithley 2000 Currentmeter). Electroluminescence spectrums are measured by SPEX CCD3000 spectrometer (from JY company, French) at room temperature under atmospheric environment. The test results are as shown in table 2.

TABLE 2 tested performances of devices.

| Device | Maximum current efficiency (cd/A) | CIEy&CIEx | Maximum external quantum efficiency (%) |
|---|---|---|---|
| Device 1 | 17.3 | 0.10 | 18.3% |
| Device 2 | 65.3 | 0.26 | 30.7% |
| Device 3 | 17.8 | 0.68 | 21.6% |

Industrial applicability: The subject matter of the present disclosure can be manufactured and used in the industry, thereby having industrial applicability.

What is claimed is:

1. A thermally activated delayed fluorescence material having red, green, or blue color, having the following structural formula:

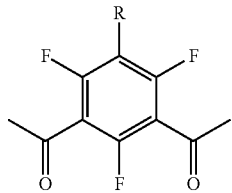

wherein, R is one of the following structural formulas:

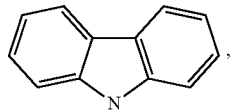

,

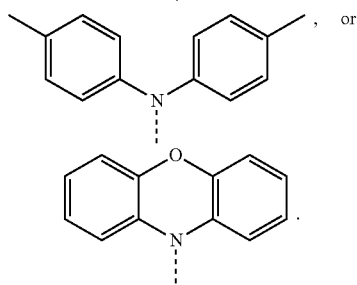

, or

.

2. A synthesis method of the thermally activated delayed fluorescence material having red, green, or blue color according to claim 1, comprising: under an inert gas protective environment, performing a Buchwald-Hartwig coupling reaction between a raw material 1 and a raw material 2 under an effect of a palladium catalyst to obtain the thermally activated delayed fluorescence material having red, green, or blue color;

wherein, the raw material 1 has the following structural formula:

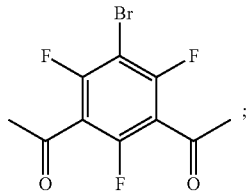 [SMILES: CC(=O)c1c(F)c(Br)c(F)c(C(C)=O)c1F]

;

the raw material 2 is one of carbazole, phenoxazine, or dimethyldiphenylamine, and a molar ratio of the raw material 1 to the raw material 2 ranges from 1:1 to 1:3.

3. The synthesis method of the thermally activated delayed fluorescence material having red, green, or blue color according to claim 2, wherein a reaction temperature of the Buchwald-Hartwig coupling reaction ranges from 80° C. to 160° C., and a reaction time thereof ranges from 12 hours to 48 hours.

4. The synthesis method of the thermally activated delayed fluorescence material having red, green, or blue color according to claim 2, wherein a reaction solvent of the Buchwald-Hartwig coupling reaction is dehydrated and deoxygenated toluene, and the palladium catalyst is at least one selected from the group consisting of palladium acetate, palladium nitrate, palladium sulfate, or palladium chloride.

5. The synthesis method of the thermally activated delayed fluorescence material having red, green, or blue color according to claim 2, wherein, after finishing the Buchwald-Hartwig coupling reaction, a reaction product is subjected to cooling, extraction, and column chromatography separation in sequence to obtain the thermally activated delayed fluorescence material having red, green, or blue color.

6. A light-emitting device, comprising an electrothermally activated delayed fluorescent device comprising the thermally activated delayed fluorescence material having red, green, or blue color according to claim 1.

7. The light-emitting device according to claim 6, wherein the electrothermally activated delayed fluorescent device comprises a substrate layer, a light-emitting layer, and a cathode layer in a stack, and a light-emitting material of the light-emitting layer is the thermally activated delayed fluorescence material having red, green, or blue color.

* * * * *